US012569196B2

(12) United States Patent
Dwarika et al.

(10) Patent No.: US 12,569,196 B2
(45) Date of Patent: Mar. 10, 2026

(54) WEARABLE PHYSIOLOGICAL MONITORING SYSTEMS AND METHODS

(71) Applicant: HEALTH CARE ORIGINALS, INC., Rochester, NY (US)

(72) Inventors: Jared Dwarika, Rochester, NY (US); Sharon Samjitsingh, Rochester, NY (US)

(73) Assignee: HEALTH CARE ORIGINALS, INC., Rochester, NY (US)

( * ) Notice: Subject to any disclaimer, the term of this patent is extended or adjusted under 35 U.S.C. 154(b) by 0 days.

(21) Appl. No.: 18/296,045

(22) Filed: Apr. 5, 2023

(65) Prior Publication Data

US 2023/0248310 A1 Aug. 10, 2023

Related U.S. Application Data

(63) Continuation of application No. 15/431,531, filed on Feb. 13, 2017, now Pat. No. 11,622,716.

(51) Int. Cl.
*A61B 5/00* (2006.01)
*A61B 5/01* (2006.01)
(Continued)

(52) U.S. Cl.
CPC .............. *A61B 5/6801* (2013.01); *A61B 5/08* (2013.01); *A61B 5/6833* (2013.01);
(Continued)

(58) Field of Classification Search
CPC ..... G16H 50/00–50/80; A61B 2503/10; A61B 5/01; A61B 5/021; A61B 5/024;
(Continued)

(56) References Cited

U.S. PATENT DOCUMENTS 4,889,132 A 12/1989 Hutcheson et al.
4,928,690 A 5/1990 Heilman et al.
(Continued)

FOREIGN PATENT DOCUMENTS

CN 102293992 A * 12/2011
WO WO-2009096630 A1 * 8/2009 ............. A61B 5/091

OTHER PUBLICATIONS

International Search Report & Written Opinion dated May 26, 2023 from PCT Application No. PCT/2023/061700.
(Continued)

*Primary Examiner* — Benjamin J Klein
*Assistant Examiner* — Vynn V Huh
(74) *Attorney, Agent, or Firm* — INNOVATION CAPITAL LAW GROUP, LLP; Vic Lin

(57) ABSTRACT

A physiological monitoring system can use physiological wearable monitors to collect and/or detect various parameters, such as cough, wheeze, heart rate, skin temperature, activity, respiration rate, skin impedance, electro-cardiogram data, blood pressure, galvanic skin response, and the like. One or more of these parameters, or other such parameters, may be used in methods in the fields of lung cancer, physiotherapy, monitoring disabled or challenged individuals, monitoring end of life conditions, monitoring breathing gas usage, monitoring patients and individual wellness, data acquisition, athletic sports monitoring, athletic sports entertainment, virtual reality feedback, telemedicine, hospital aid, illness detection and its severity, and public service, as examples. Such methods can use data from one or more wearable devices with the appropriate data processing to present the user or healthcare provider with the appropriate analysis.

5 Claims, 14 Drawing Sheets

(51) Int. Cl.

| | |
|---|---|
| *A61B 5/021* | (2006.01) |
| *A61B 5/024* | (2006.01) |
| *A61B 5/08* | (2006.01) |
| *A61B 5/145* | (2006.01) |
| *A61B 5/16* | (2006.01) |
| *A61B 5/318* | (2021.01) |
| *A63F 13/212* | (2014.01) |

(52) U.S. Cl.
CPC .............. *A63F 13/212* (2014.09); *A61B 5/01* (2013.01); *A61B 5/021* (2013.01); *A61B 5/024* (2013.01); *A61B 5/0816* (2013.01); *A61B 5/14542* (2013.01); *A61B 5/318* (2021.01); *A61B 5/742* (2013.01); *A61B 2503/10* (2013.01); *A63F 2300/8082* (2013.01)

(58) Field of Classification Search
CPC ..... A61B 5/08; A61B 5/0816; A61B 5/14542; A61B 5/165; A61B 5/318; A61B 5/486; A61B 5/6801; A61B 5/6833; A61B 5/742; A63F 13/212; A63F 2300/8082
See application file for complete search history.

(56) References Cited

U.S. PATENT DOCUMENTS

| | | | |
|---|---|---|---|
| 7,680,523 B2 | 3/2010 | Rytky | |
| 2004/0186390 A1* | 9/2004 | Ross ...................... | A61B 5/083 |
| | | | 600/532 |
| 2007/0100213 A1* | 5/2007 | Dossas ............... | A61B 5/14542 |
| | | | 600/509 |
| 2008/0288026 A1 | 11/2008 | Cross et al. | |
| 2010/0228113 A1 | 9/2010 | Solosko et al. | |
| 2011/0035158 A1* | 2/2011 | Banos .................. | A61B 5/0836 |
| | | | 73/23.3 |
| 2011/0144470 A1 | 6/2011 | Mazar et al. | |
| 2015/0088007 A1 | 3/2015 | Bardy et al. | |
| 2015/0257654 A1 | 9/2015 | Bennett-Guerrero | |
| 2016/0100808 A1* | 4/2016 | Anbarani ............. | A61B 5/7282 |
| | | | 600/536 |
| 2016/0361026 A1 | 12/2016 | Sarkar et al. | |
| 2017/0071506 A1 | 3/2017 | Dwarika et al. | |
| 2018/0049653 A1 | 2/2018 | Husheer et al. | |
| 2019/0290150 A1 | 9/2019 | Felix et al. | |
| 2020/0188697 A1 | 6/2020 | Kabrams et al. | |
| 2021/0063434 A1 | 3/2021 | Laput et al. | |

OTHER PUBLICATIONS

International Preliminary Report on Patentability (Chapter II) dated May 17, 2024 from PCT Application No. PCT/2023/061700 (24 pages).

* cited by examiner

~100

~102

DISPOSE A WEARABLE ON A FIRST RESPONDER

~104

MONITOR CHANGING BODY FUNCTIONS OF THE
FIRST RESPONDER

~110

~112

DISPOSE A WEARABLE ON A USER NEEDING
BREATHING GAS MONITORING

~114

SUPPLY BREATHING GAS TO MEET USER DEMAND
BASED ON WEARABLE MEASUREMENTS

~116

MONITOR PATIENT FOR PROPER ANESTHESIA
GAS APPLICATION

WEARABLE PHYSIOLOGICAL MONITORING SYSTEMS AND METHODS

CROSS-REFERENCE TO RELATED APPLICATIONS

This application is a continuation of U.S. patent application Ser. No. 15/431,531, filed Feb. 13, 2017, the contents of which are herein incorporated by reference.

BACKGROUND OF THE INVENTION

1. Field of the Invention

Embodiments of the invention relate generally to respiratory and physiological monitoring systems. More particularly, the invention relates to respiratory and physiological monitoring systems and wearable devices usable in methods in various fields, such as medical, athletic, public safety, wellness, entertainment, data acquisition, and the like.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Physiological sensors have long been known and widely used for certain medical and health related applications. Various physiological sensors embedded in textile or garments, sometimes called portable or wearable sensors, have been described before in publications and patents (Portable Blood Pressure in U.S. Pat. No. 4,889,132; Portable device for sensing cardiac function in U.S. Pat. No. 4,928,690; Heart rate monitor in garment in U.S. Pat. No. 7,680,523 B2). The term "wearable sensors" is now commonly used to describe a variety of body-worn sensors to monitor activity, environmental data, body signals, biometrics, health related signals, and other types of data.

As used herein, "plethysmography", and its derivative words, is the measurement of changes in volume within an organ or whole body, or a cross-sectional area of the body when the body is constant in height. "Inductive plethysmography" is a plethysmographic measurement based on determination of an inductance or a mutual inductance. A "plethysmographic signal" is a signal generated by plethysmography, and specifically by inductive plethysmography. The cross-sectional area of the body measured by a plethysmograph may include, singly or in combination, the chest, abdomen, neck, or arm, for example.

Respiration measurements can provide insight into an individual's wellbeing. Respiration measurements can be indicative of physiological and/or mental states of an individual, as well as prognostic with regard to diagnosis of medical conditions. For example, respiration measurements can provide insight into an individual's stress levels, and can be evidential of more serious pulmonary disorders, such as disorders associated with chronic obstructive pulmonary disease (COPD) and asthma.

Traditionally, however, respiration monitoring has occurred in a clinical setting, contributing to the developing of respiration monitoring devices that are non-ambulatory, lack portability, and are difficult to use. Other respiration monitoring devices include those that are tethered to another device for full functionality.

These conventional devices include smart devices (such as smartphones) tethered to sensors with or without data-loggers where meaningful processing of the sensor data occurs on the smart device. Present shortcomings include wearables that lack the ability to detect, data-log and analyze acoustic physiological signals, wearables that have to be embodied in vests or some other system larger than the intended wearable, wearables that have wired or wireless connections to another component or device housed separately from the wearable, and wearables that attempt to detect signals that infer that the acoustic physiological signals are present.

While wearables have been used for basic measurements, measurements taken from one wearable are often analyzed in a vacuum, without regard to other parameters that may be sensed or detected. This limits the usability of a physiological wearable. Moreover, many wearables provide specific data without any data analysis that may be useful for detecting certain conditions, monitoring individuals, detecting personal wellness, monitoring athletes, providing entertainment, and the like.

In view of the foregoing, it is clear that there is a need for methods for using physiological monitoring systems for purposes beyond which are currently contemplated in the art.

SUMMARY OF THE INVENTION

Embodiments of the present invention provide a method for measuring at least one physiological parameter from a user having a need to measure or monitor the at least one physiological parameter comprising disposing a wearable on a user; and measuring the at least one physiological parameter of the user with at least one sensor disposed in the wearable, wherein the step of measuring the at least one physiological parameter provides collected data that is provided to an algorithm for detection of one or more medical issues.

Embodiments of the present invention provide a method for measuring at least one physiological parameter from a user having a need to detect or monitor a lung cancer condition comprising disposing a wearable on a user; and measuring the at least one physiological parameter of the user with at least one sensor disposed in the wearable, wherein the step of measuring the at least one physiological parameter provides collected data that is provided to an algorithm for detecting or monitoring a lung cancer condition.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figures 1A, 1B, 1C:
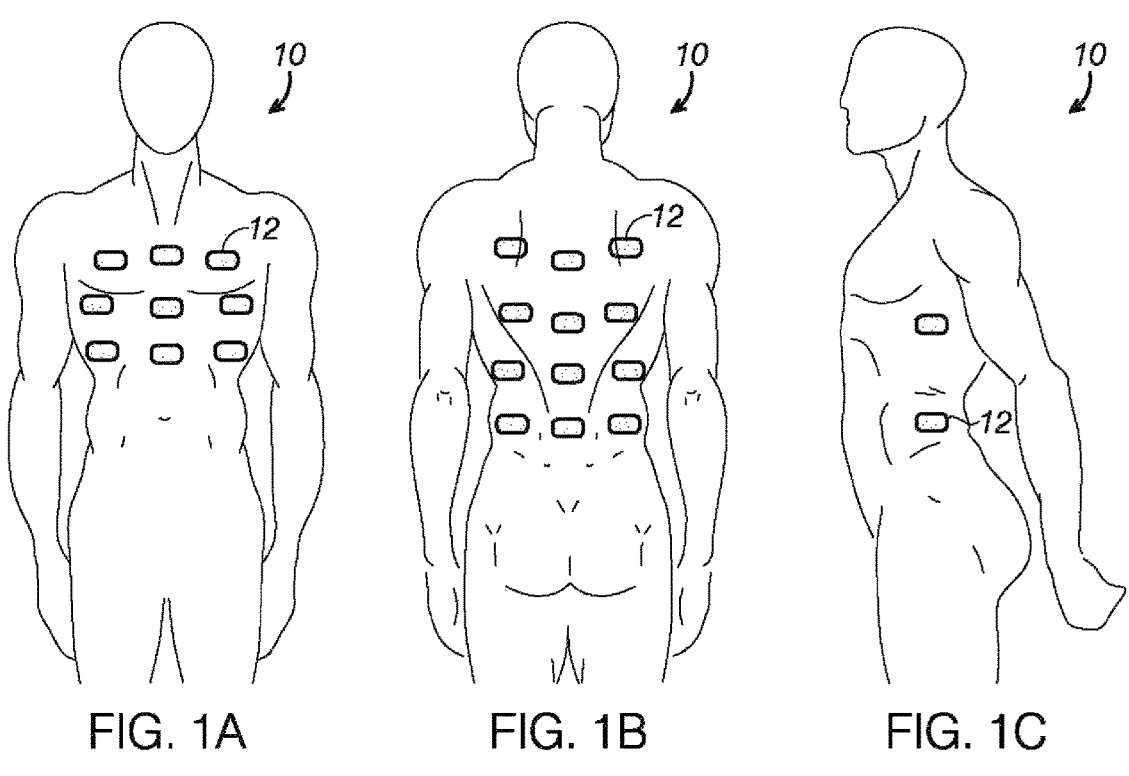
FIGS. 1A through 1C illustrate various placement options for one or more wearables on a user to perform methods according to exemplary embodiments of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Devices or system modules that are in at least general communication with each other need not be in continuous communication with each other, unless expressly specified otherwise. In addition, devices or system modules that are in at least general communication with each other may communicate directly or indirectly through one or more intermediaries.

A "computer" or "computing device" may refer to one or more apparatus and/or one or more systems that are capable of accepting a structured input, processing the structured input according to prescribed rules, and producing results of the processing as output. Examples of a computer or computing device may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

"Software" or "application" may refer to prescribed rules to operate a computer. Examples of software or applications may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Python, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). The program code may also be distributed among a plurality of computational units wherein each unit processes a portion of the total computation.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Web sites comprise a collection of connected, or otherwise related, webpages. The combination of all the web sites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASHEEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

Embodiments of the present invention may include apparatuses for performing the operations disclosed herein. An apparatus may be specially constructed for the desired purposes, or it may comprise a general-purpose device selectively activated or reconfigured by a program stored in the device.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory or may be communicated to an external device so as to cause physical changes or actuation of the external device.

Broadly, embodiments of the present invention provide a physiological monitoring system that can use physiological wearable monitors to collect and/or detect various parameters, such as cough, wheeze, heart rate, skin temperature, activity, respiration rate, skin impedance, electro-cardiogram data, blood pressure, galvanic skin response, and the like. One or more of these parameters, or other such parameters, may be used in methods of the present invention in the fields of lung cancer, physiotherapy, monitoring disabled or challenged individuals, monitoring end of life conditions, monitoring breathing gas usage, monitoring patients and individual wellness, data acquisition, athletic sports monitoring, athletic sports entertainment, virtual reality feedback, telemedicine, hospital aid, illness detection and its severity, and public service, as examples. Such methods can use data from one or more wearable devices with the appropriate data processing to present the user with the appropriate analysis.

The wearables usable in the methods of the present invention can take various forms. In some embodiments, the wearable may be placed directly in contact with the human body, such as by adhesive to the wearer's skin. The description below describes some embodiments of a wearable usable in the methods of the present invention. The methods discussed herein, however, are not limited to any particular type of wearable, mounting location, or mounting configuration.

FIGS. 1A through 1C illustrate an exemplary wearable 12 attached to a user 10. Typically, a single wearable 12 can be attached and includes multiple functions, as discussed below, built therein. In some embodiments, more than one wearable 12 may be worn by the user at different locations. For example, where it is desired to detect wheezing or rales in each lung separately, two wearables 12 may be worn at each lung location. FIGS. 1A through 1C show examples of various locations where one or more of the wearables 12 may be positioned on the body of the user 10. Of course, other locations outside of those specifically shown are contemplated within the scope of the present invention.

Figure 2:
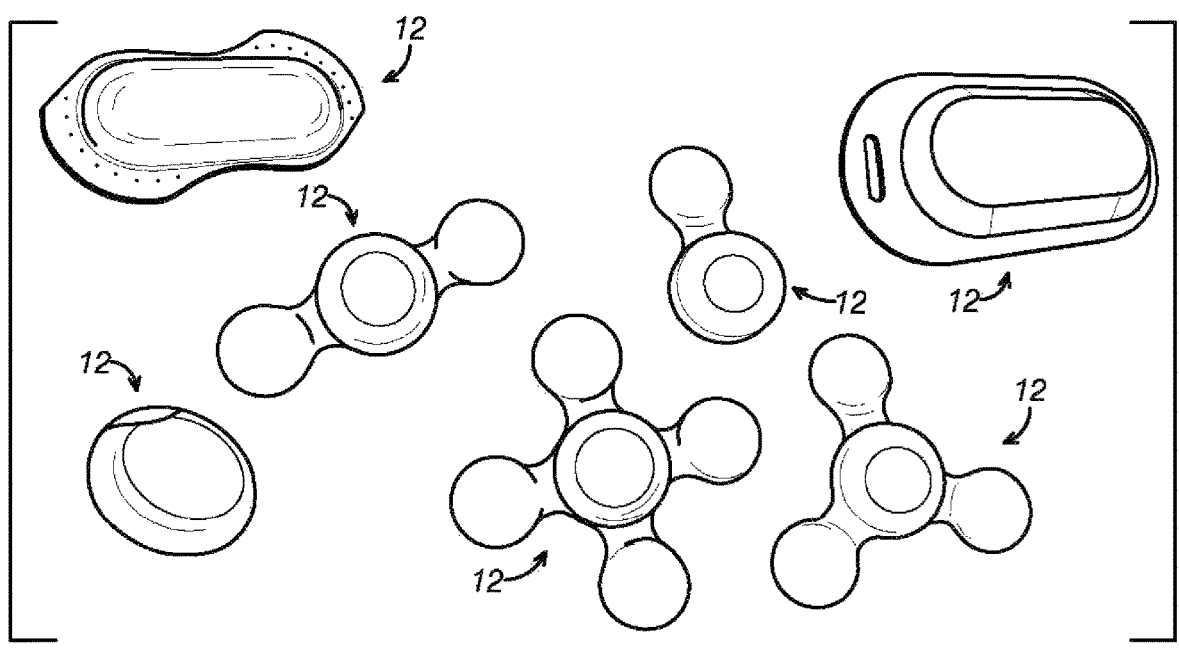
FIG. 2 illustrates top perspective views of various configurations for the wearables shown in FIGS. 1A through 1C.

The wearable 12 can take the form of various shapes or sizes. FIG. 2 shows examples of various shapes and sizes of the wearable 12. In some embodiments, the specific size and shape may depend on the specific application, the desired wear location, activity level of the user, or the like.

Figure 3:
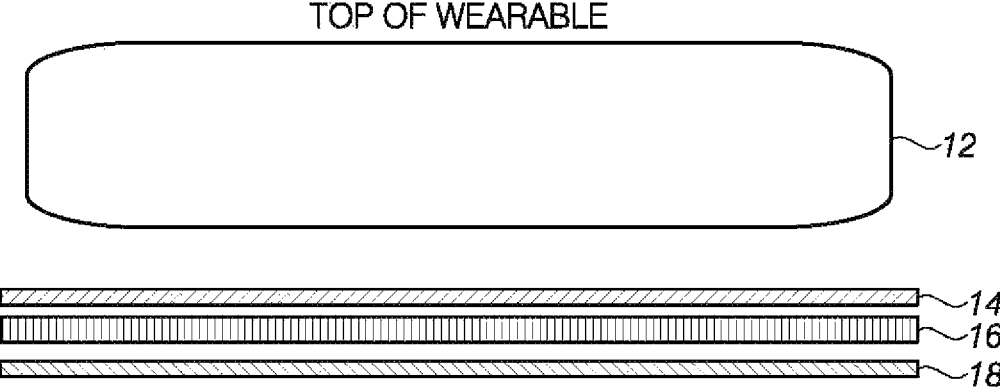
FIG. 3 illustrates a side view of a wearable usable for performing methods according to exemplary embodiments of the present invention.

Referring to FIG. 3, when the wearable 12 is attached to the skin surface, the wearable 12 may be attached to a mounting material 16 via an adhesive 14, for example. The mounting material 16 can then be attached to the skin of the user 10 with an adhesive 18 for bonding with the skin.

Figure 4:
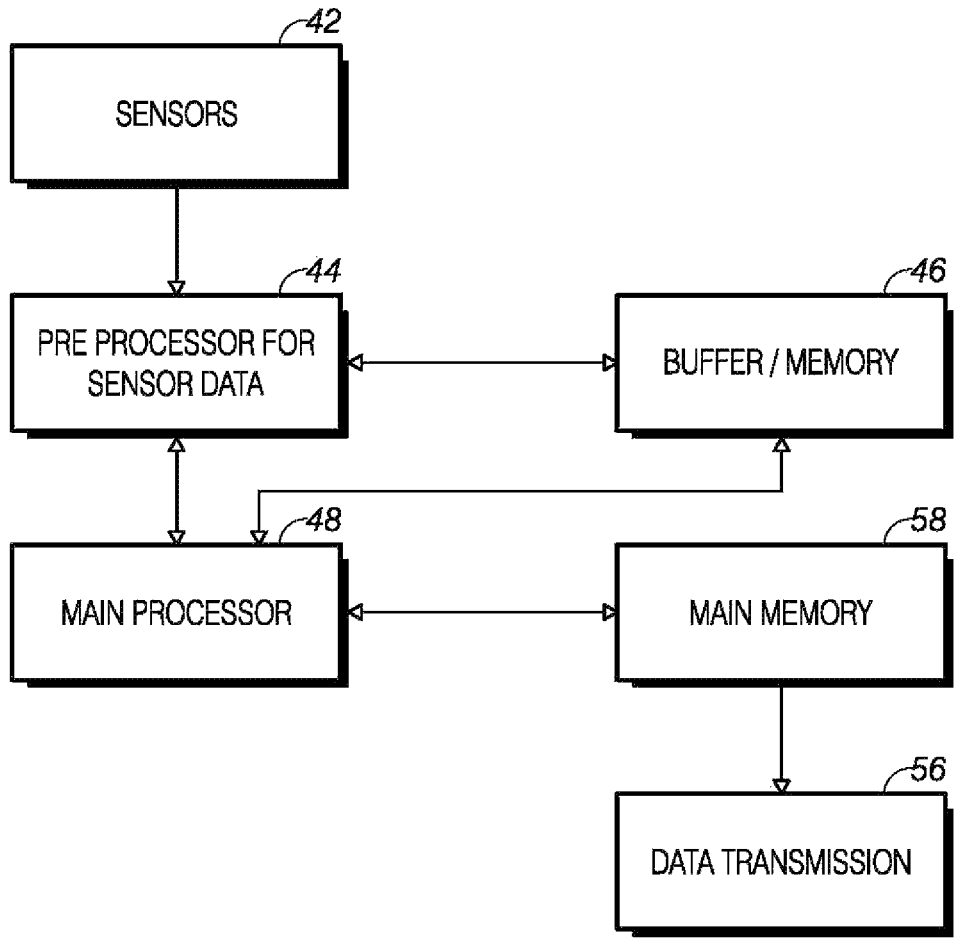
FIG. 4 illustrates exemplary processing performed within a wearable according to an exemplary embodiment of the present invention.
Figure 5:
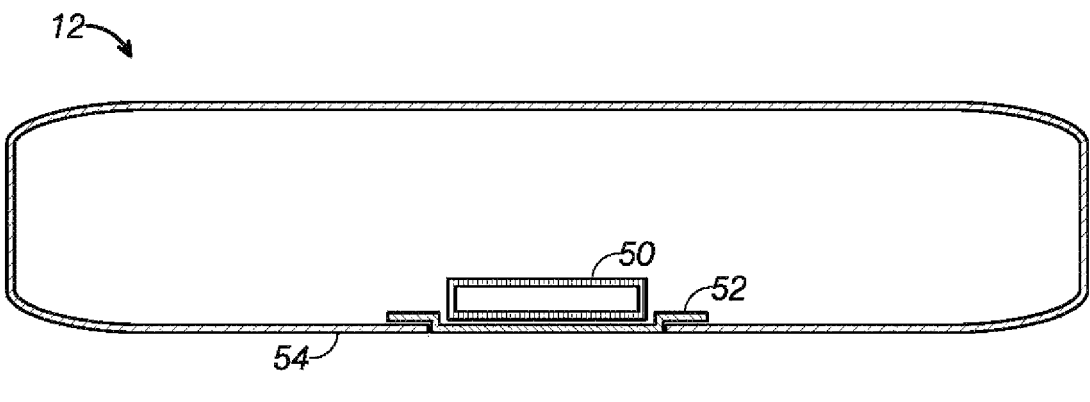
FIG. 5 illustrates a cross-sectional view of a wearable in a vicinity of an acoustic sensor, according to an exemplary embodiment of the present invention.

Referring now to FIGS. 4 and 5, the wearable 12 can include various components and/or modules. The wearable can include one or more sensors 42, typically a plurality of sensors 42 for detecting various physiological parameters of a wearer. The sensors 42 can include one or more acoustic sensors 50 which may be embedded in a protective layer 52 that facilitates sound transfer through a housing 54 of the wearable 12. In some embodiments, the wearable 12 can further include a pre-processor 44 for sensor data, a buffer/memory 46, a main processor 48, and a main memory 58. The wearable 12 may also include an alert generation mechanism (not shown) to alert the user of a significant change in measured physiological or acoustic parameters as compared to a baseline. In some embodiments, the alert generation may be performed by an external device receiving a signal from the wearable 12. Each of these components will be discussed in greater detail below.

The sensors 42 in a sensor array can include one or more of the following: an accelerometer, a gyroscope, a microphone (where the microphone could be any of capacitive, piezoelectric, electro-magnetic, electret, and the like), temperature sensor (where the temperature sensor could be any of thermocouple, RTD, thermistor, infrared, and the like), vibration sensor, optical sensor (where the optical sensor can be configured for various applications), sensors for measuring blood oxygen saturation, sensors for measuring blood pressure, sensors for measuring skin impedance, sensors for measuring galvanic skin response and sensors for measuring the electrical potential of the body. Some or all sensors described above can be used according to the desired accuracy and depth of information.

In some embodiments, the array of sensors 42 capitalizes on processing by the pre-processor 44. Typically, the pre-processor 44 may be located on board the sensor 42 and/or sensor array. The extent of the pre-processing ranges from simple signal conditioning to pattern and event recognition.

Additionally, the sensor 42 and/or sensor array can include the ability to transfer data directly to memory (into the buffer/memory 46) for storage without engaging either the pre-processor 44 and/or the main processor 48.

Additionally, signals from the sensors 42 may be kept separate or be combined within the sensor array to form a fusion of sensor signals.

The pre-processors 44 can be of the low power variety. While the sensors 42 may not be classified as low power, they can be connected to dedicated low power pre-processors 44 for initial signal treatment.

In some embodiments, reduced power consumption can be achieved by having the sensor data be processed at dedicated low power pre-processors 44 at first and events of interest are then stored directly to memory 58 and/or the buffer/memory 46. After a period of time and/or memory count, the main processor 48 can come alive to process the signals. The reasoning is that the main processor 48 uses the most power and therefore, should run for the least amount of time possible. The main processor 48 uses the most power because it operates the main functions of the wearable 12 and the processing algorithms, for example. The pre-processor 44 on a sensor only runs a basic screening algorithm and supports memory transfer thereby qualifying it as a low power application. In other embodiments, depending on the power demands of the wearable 12, the sensor data may be processed as it is received, or may simply be stored in the memory and transferred as raw data to a separate computing device for processing and/or analysis as discussed in greater detail below.

The wearable 12 can transmit data via a data transmission module 56 wirelessly according to a schedule. The next major power consuming component, a radio transmitter (part of the data transmission module 56), can be made into a low power component due to its very low duty cycle. While the transmitter operates to full design specifications, it does so for brief moments, resulting in reduced power consumption. By processing the signals onboard, the device derives a result and this result is simple to display, manipulate, transmit, and the like, as it is significantly less than having to output raw data streams. Hence the transmission of this brief result constitutes the extremely low duty cycle.

Additionally, the power management algorithm is able to shed functions as battery power runs low, thereby achieving a longer runtime on the remaining power.

Communication with external devices and environment for setup, information relaying, upgrades, and the like, can be done via a physical port (not shown, but may be, for example a micro and/or mini USB port), wirelessly via Bluetooth Low Energy, Bluetooth regular, Machine-to-machine (cellular based), Body Area Networks, ZigBee, and the like, and the method is determined by the application. Wireless communications may be direct to an end point or a relay unit and, as such, would incorporate the requisite antenna. One or more communication methods may be built-in to the wearable 12.

While the wearable 12 is intended to be worn against the body and while there is no substantial evidence to show that the above radio communication causes bodily harm, the wearable 12 may incorporate an added step to reduce exposure. Wireless infrastructure comes alive on a schedule that is user settable but ranging from once every fifteen minutes to once every two hours, for example. By having such a procedure, the body is exposed to radio signals emanating from the device only at those times. Further still, the length of the transmission during these times are estimated at no more than ninety seconds, for example, at design power.

The communication range of the wearable 12 depends on its operation. For setup and visualization of the output data, the wearable 12 can be connected to a smartphone or smartdevice via Bluetooth and or Bluetooth Low Energy architecture, for example. For setup and visualization of output data when a smartphone or smartdevice is not available or out of range, the device can connect via a cellular service to an end point, relay unit or data service. In this instance, the data can be re-routed to a smartphone or smartdevice and can also be available via a web portal.

Regardless of mode, the device can send alerts via all communication modes thereby increasing the range beyond Body Area Networks, Bluetooth and BTLE, node to node Wi-Fi, or the like.

Additionally, the wearable 12 can be designed to accommodate various adhesives being stuck to it for subsequent adhesion to the skin. The lightweight characteristics of the wearable 12 means that adhesives, such as adhesives 14, 18 of FIG. 3, can be of the easy to peel variety.

As discussed above, the wearable 12 can include a main processor 48 or processors to control the operation thereof, execute the processing of signals, execute algorithms utilizing signal data and or stored data, execute power management, memory management, user interactions, wireless communications and any other processes and or functionality.

The processor 48 may be of the low power consumption variety and when it is such, the device has longer runtimes. Additionally, the processor 48 can be set to execute programs or applications on demand rather than having to execute an instruction set comprising most or all of the functionality.

Additionally, the programs or applications as well as the processor's operating system may be modified, changed or updated even after being set into operation. Such an approach allows for the device to be adopted for many uses as well as capitalize from automatic remote bug fixes and or functionality enhancement.

By processing the signals onboard, the wearable 12 derives a result that is simple to display, manipulate, transmit, and the like, as it is significantly less than having to output raw data streams. In some embodiments, where onboard processing is not required, the sensor data may be preprocessed by the wearable 12 or may be sent directly to an external computing device for processing. In some embodiments, sensor data may be sent via the internet to a remote station for processing and the data may be stored in a database.

When the wearable 12 is being worn, it doubles over as an electronic stethoscope but more importantly, picks up sounds outside of human hearing which is important for recognizing patterns. The versatility of the algorithms means that the wearable 12 could be programmed to detect and record almost any acoustic physiological symptom or event that could be collected from the region of the upper torso.

The wearable 12 can be further equipped for detecting and recording heartbeat rate via audio and vibration methods. The wearable 12 can be further equipped for detecting and recording body skin temperature via any of thermocouples, thermistors, infrared, and the like. The wearable 12 can be further equipped with sensors for various other purposes, as described above.

While the above describes various embodiments of wearables usable in methods of the present invention, other wearables, as may be known in the art, may be incorporated in the methods of the present invention, as described below and in the accompanying claims.

Lung Cancer

In 5-15% of patients, an early acute pneumonitis, which is characterized by a non-productive cough, fever and dyspnea on exertion, develops 2-12 weeks after radiotherapy. It is thought that the early onset of symptoms is indicative of a more serious and protracted clinical course. In some cases, fibrosis spreads outside the radiation field, even to the contralateral lung, progressing to acute, often fatal, respiratory failure. Therefore, it would be very important if one were able to anticipate the occurrence of severe radiation pneumonitis (RP) spreading beyond the radiation field.

Figure 6:
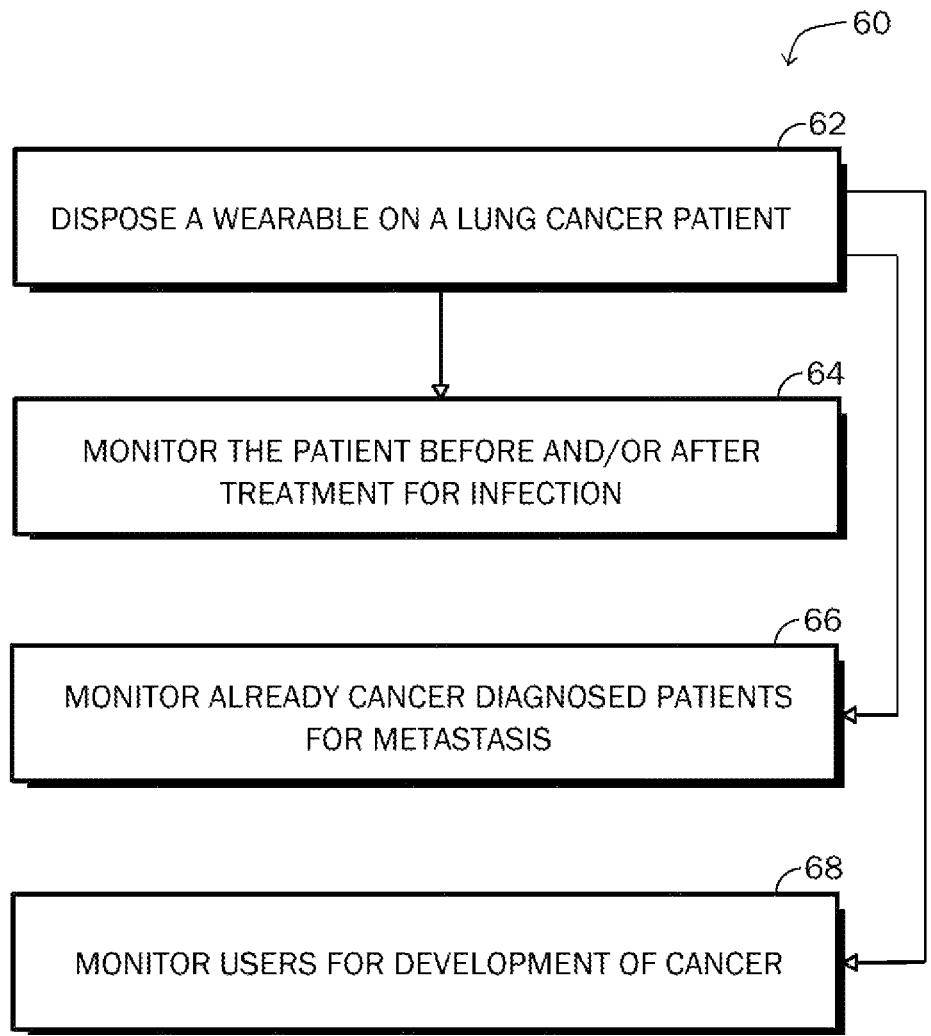
FIG. 6 illustrates an exemplary method for using a wearable in cancer applications according to an exemplary embodiment of the present invention.

Referring now to FIG. 6, a method 60 of the present invention using wearable technology may be used in various areas in the field of lung cancer. One or more wearable devices may be disposed on a patient, or user, in step 62. In some embodiments, a wearable may be used to monitor a patient during and after treatment (e.g., chemotherapy and/or radiotherapy) for infections (e.g., radiation pneumonitis), in step 64, until they have passed into a low risk period.

Metastatic lung cancer is a life-threatening condition that develops when cancer in another area of the body metastasizes, or spreads, to the lung. Cancer that develops at any primary site can form metastatic tumors. These tumors are capable of metastasizing to the lungs.

The symptoms of metastatic lung cancer can include a persistent cough, coughing up blood or bloody phlegm, chest pain, shortness of breath, wheezing, weakness and sudden weight loss.

Methods of the present invention may use wearable technology to monitor the already cancer-diagnosed patient to see if the cancer is metastasizing, in step 66, as evidenced by increases in some of certain parameters, such as those described in the above paragraph, monitored by the wearable.

Methods of the present invention that use wearable technology can also be used to monitor a patient, whether at risk for cancer or undiagnosed, to see if they are potentially developing cancer, in step 68, by identifying the parameter trends described above with respect to cancer metastasis, for example.

Physiotherapy

Physiotherapy, or physical therapy, is the treatment or management of a physical disability, malfunction, or pain by physical techniques, as exercise, massage, hydrotherapy, and the like.

Figure 7:
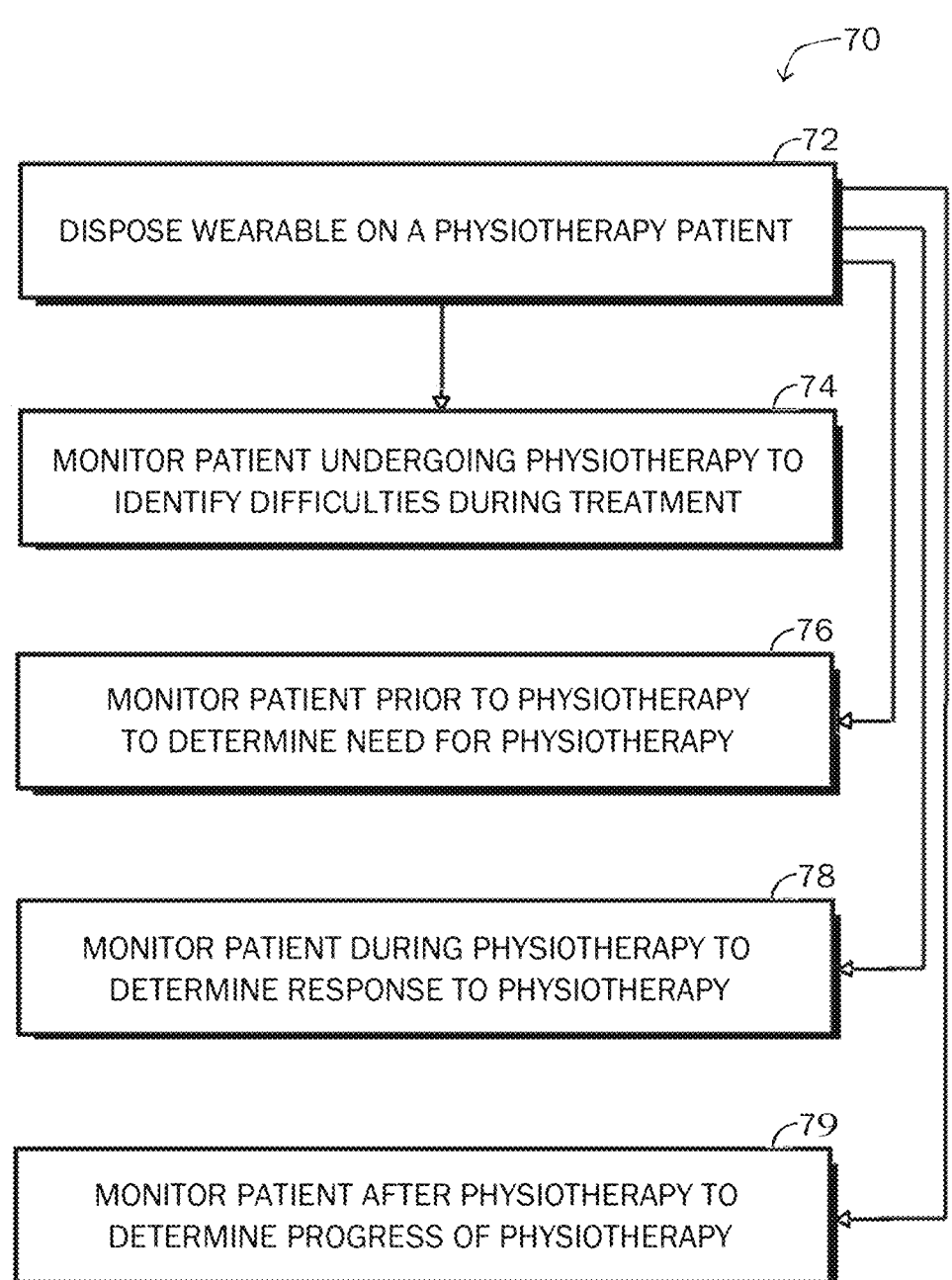
FIG. 7 illustrates an exemplary method for using a wearable in physiotherapy applications according to an exemplary embodiment of the present invention.

Referring to FIG. 7, a method 70 of the present invention can use wearable technology, disposed on a patient in step 72, to monitor the patient undergoing physiotherapy to identify, independently of the patient themselves, if they are experiencing difficulties brought on by the therapy or otherwise in step 74, as can be inferred by the parameters collected.

In some time of physiotherapy, e.g., breathing requirements, the monitoring of someone prior to (step 76), during (step 78) and after (step 79) therapy may be useful to see if they are in need of therapy, how they are responding to therapy, and how they are progressing once therapy is concluded, respectively.

Disabled and Challenged

Some individuals may not be able to properly express themselves to let others know if they are developing or experiencing distress. For example, autistic persons may lack the ability to verbally express themselves. Intellectual disability is defined as mental retardation or impairment in the areas of development or cognitive activities. Intellectual disability may be defined as a disability characterized by significant limitations both in intellectual functioning and in adaptive behavior, which covers many everyday social and practical skills. This disability originates before the age of 18. Because of intellectual disabilities many people are not able to express their pain verbally. Therefore, the skills of nursing staff are important to identify and manage pain in this vulnerable group of people. Pain assessment and management have been the focus of interest internationally in several scientific fields. However, research into pain assessment among non-communicating intellectually disabled people has been very limited.

Figures 8, 9:
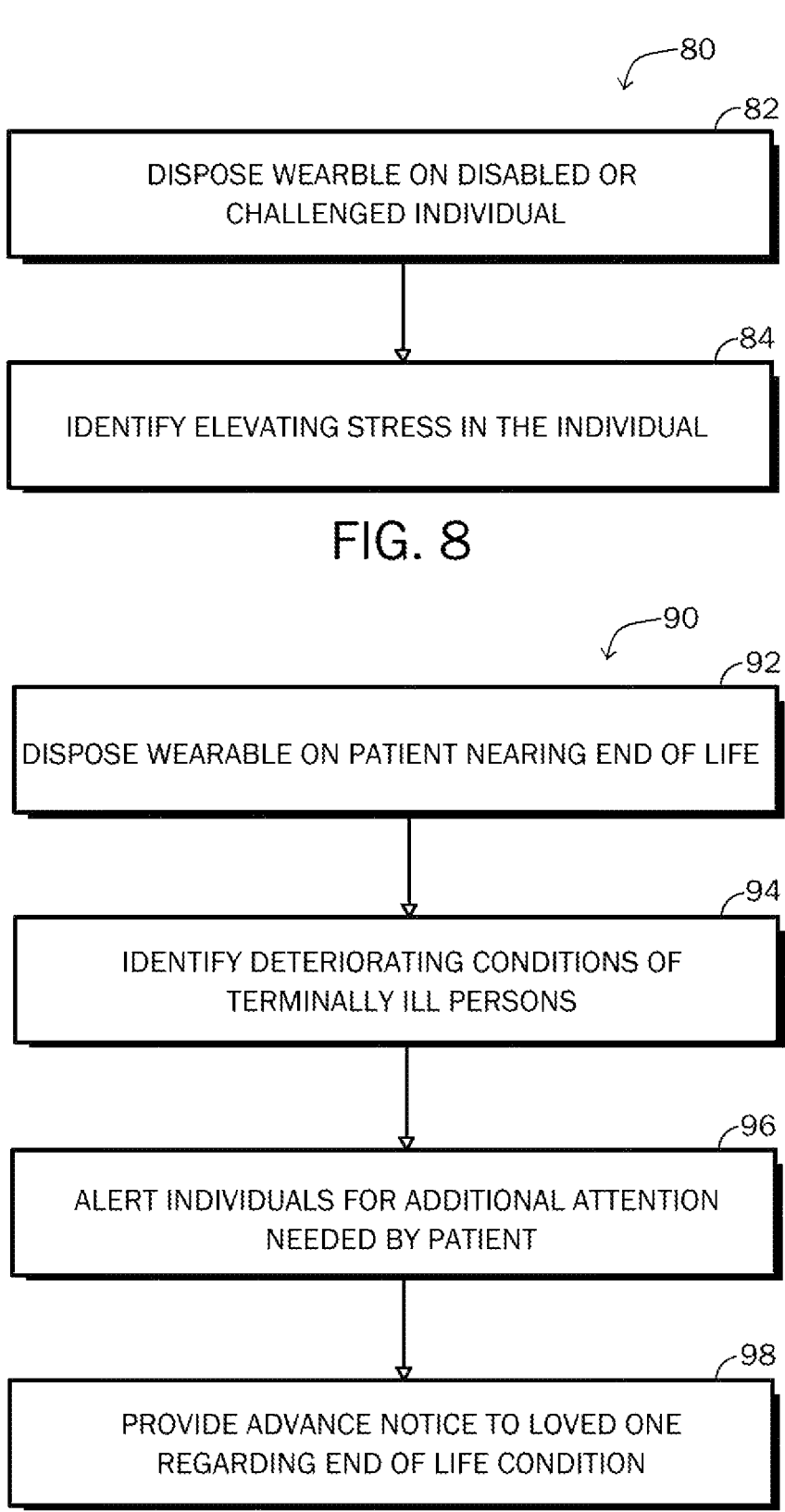
FIG. 8 illustrates an exemplary method for using a wearable in disabled/challenged individual applications according to an exemplary embodiment of the present invention.
FIG. 9 illustrates an exemplary method for using a wearable in end of life applications according to an exemplary embodiment of the present invention.

Referring to FIG. 8, a method 80 of the present invention can use wearable technology, disposed on an individual in step 82, to monitor disabled or challenged individuals for elevating stress, in step 84, due to their current condition. For example, a wearable could be used to detect when such individuals are experiencing distress as can be inferred from the measured parameters, e.g., an asthma attack. Many times, such disabled or challenged persons are mobile and independent, but lack the ability to express themselves properly. By monitoring certain parameters, such as respiration, heart rate, diaphoresis, or the like, the methods of the present invention can detect and manage distress in these individuals.

End of Life

Referring now to FIG. 9, a method 90 of the present invention can use wearable technology, disposed on a person in step 92, to identify deteriorating conditions of terminally ill persons or elderly, in step 94, where such conditions are typical with being very close to the end of life. When such conditions are detected, the methods of the present invention may be used to call for additional attention in step 96, to provide advanced notice to loved ones in step 98, e.g., to head to the bedside, and the like. These conditions that may indicate approaching the end of life can include decreased blood pressure, irregular breathing, increased restlessness, cold feet and hands, weak pulse and congestion, for example.

Public Safety

Safety devices are used by public safety personnel, such as by firefighters, to detect, for example, lack of movement. Firefighters currently often wear a device on their person that will sound an alert if the person is not moving for a certain period of time. However, by the point of non-movement, a firefighter may already be physiologically distressed to a point of damage.

Figures 10, 11:
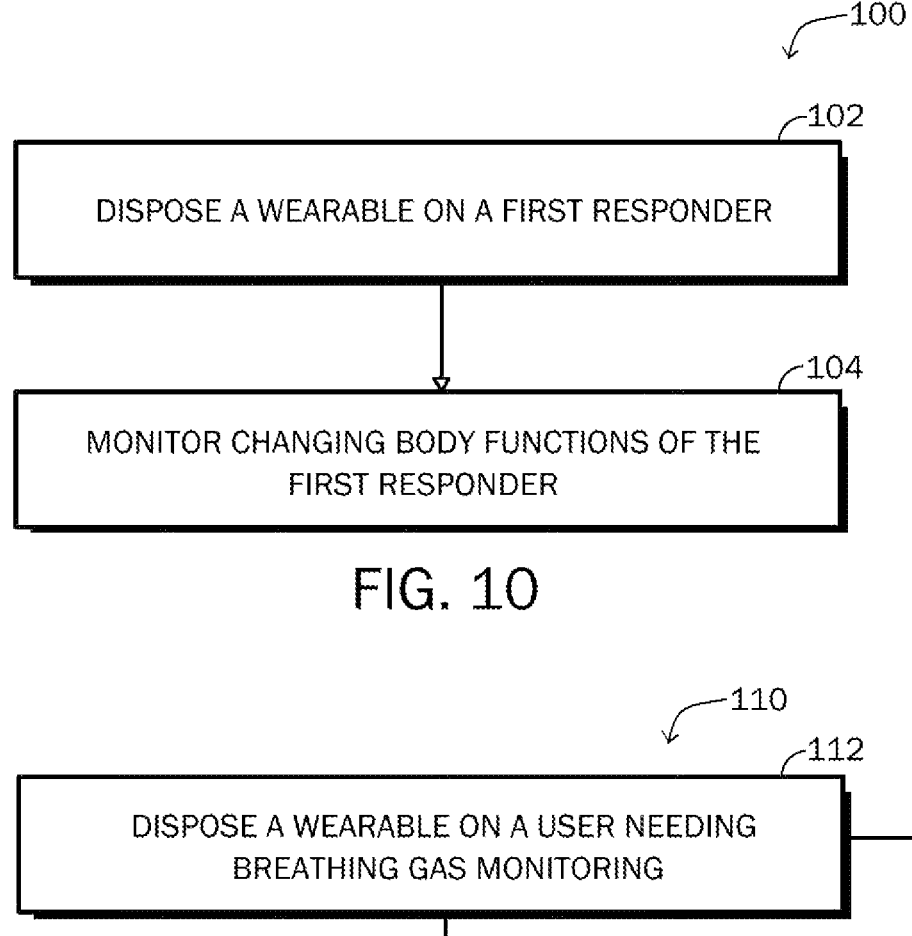
FIG. 10 illustrates an exemplary method for using a wearable in public safety/first responder applications according to an exemplary embodiment of the present invention.
FIG. 11 illustrates an exemplary method for using a wearable in breathing gas monitoring applications according to an exemplary embodiment of the present invention.

Referring to FIG. 10, a method 100 of the present invention may use wearable technology, disposed on a first responder in step 102, to monitor changing body functions of a firefighter, in step 104, to determine the stresses from inhaled gases temperature change fatigue, physical exertion, and the like, before they are self-aware or, in the case of gases, before a monitor could register above a sensor threshold. This can enable decisions that may reduce the risk of injury to him or her. In addition to firefighters, these methods may be used for any first responder, hazardous material response technicians, and the like.

Breathing Gas Usage

Referring to FIG. 11, a method 110 of the present invention can use wearable technology, disposed on a user needing breathing gas monitoring in step 112, as a monitoring device working in tandem with another device that controls the amount of breathable gas that should be made available to the user based on information inferred from the parameters collected by the wearable in step 114.

For example, an increase in activity level, and possibly respiration and heartbeat rate, could signal the need for more gas volume due to potential increase in depend (e.g., for oxygen). This allows the amount of gas made available to suit demand, thereby possibly reducing waste or complications with excessive or insufficient or inappropriate mixtures and the like.

This application could be extended into monitoring during some surgeries for more effective application of anesthesia gases in step 116, e.g., procedures at underequipped facilities, such as for cosmetic surgery.

This application may also be used for other applications where gas mixtures and/or appropriate oxygen delivery is required. For example, scuba divers may be monitored to measure blood gases and adjust breathing gas mixtures accordingly, thereby assuring proper mixtures for deep dives, long dives and the like. Further, babies in distress may need supplemental oxygen, however too much oxygen could result in brain injury or blindness. Therefore, methods of the present invention can measure parameters, such as an infant's respiration, heart rate, blood oxygen saturation, and the like, to adjust the amount of supplemental oxygen provided.

Patient Monitoring

Figure 12:
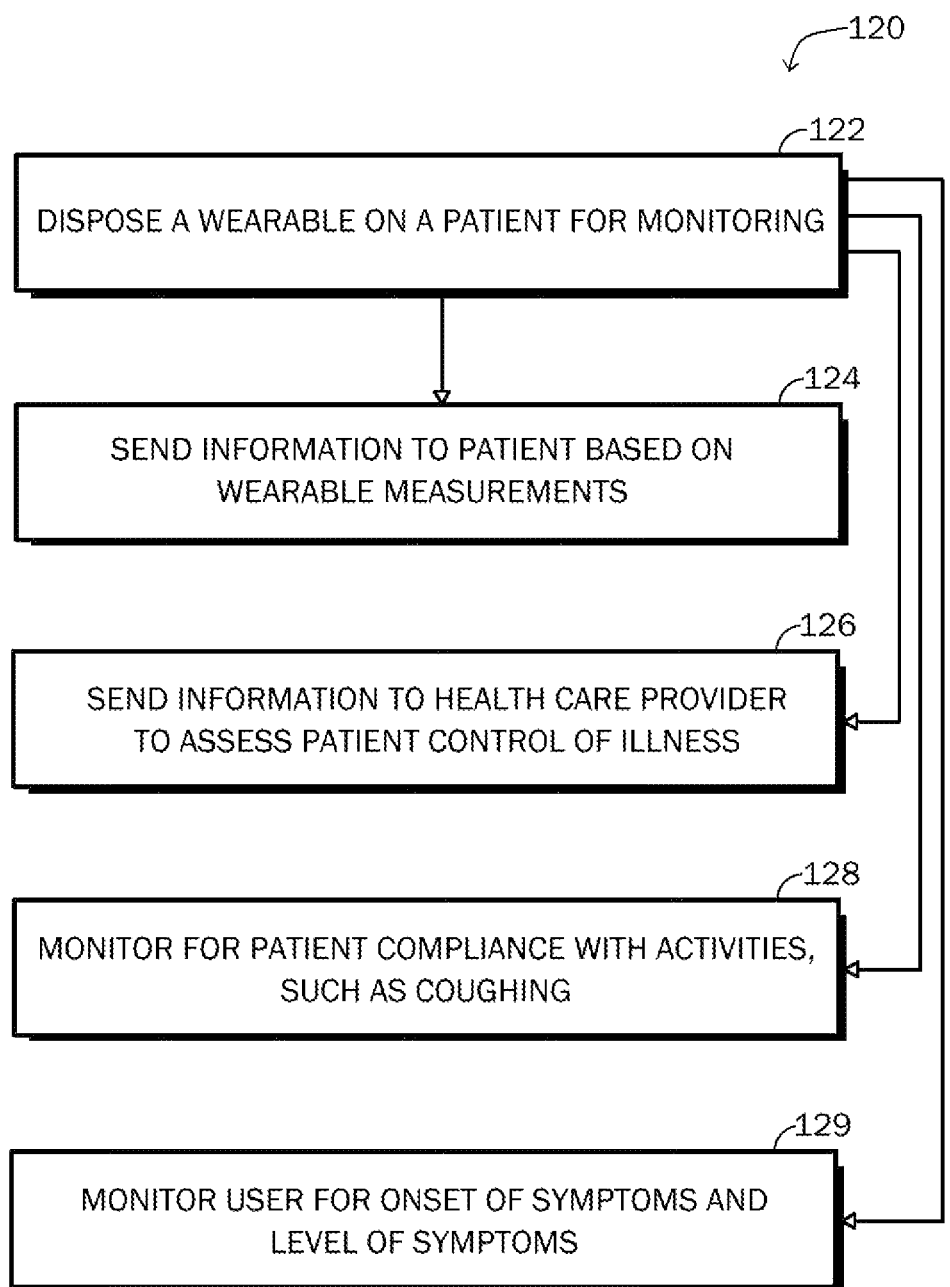
FIG. 12 illustrates an exemplary method for using a wearable in patient monitoring applications according to an exemplary embodiment of the present invention.

Referring to FIG. 12, a method 120 of the present invention can assist patients with illnesses to achieve control by utilizing the data collected by the wearable device disposed on the patient in step 120. Individual attention could be sent to the patent periodically in step 122, such as once a day. This information could include details on how well they are controlling their symptoms, what they can do to better control their condition, and the like. This information can be generated within the wearable via an algorithm running on the wearable, or may be generated and/or used by a third party that receives sensor data from the wearable. Such patient monitoring may be useful for a healthcare provider to assess the patient's control of their illness and provide data for the healthcare provider, in step 126, to adjust medication dosage, provide different and/or different medication, or the like.

Along these lines, methods of the present invention not only include monitoring a patient or user to identify increases in symptom levels where lower levels are preferred, but also for decreases in levels where elevated levels are preferred. For example, coughing is often encouraged after some treatment types or for some illnesses. The methods of the present invention, in step 128, can monitor the patient to be assure that these activities are being performed and/or such values being measured.

Methods of the present invention can use wearable technology for various respiratory illnesses in identifying symptom levels, early onset of symptoms before the wearer is aware, in step 129, providing alerts based on set points and/or baselines, and the like. These illnesses can include other non-respiratory illnesses, including those illnesses that result in a change that can be identified by changes in the measured parameters of the wearable.

Wellness

Figure 13:
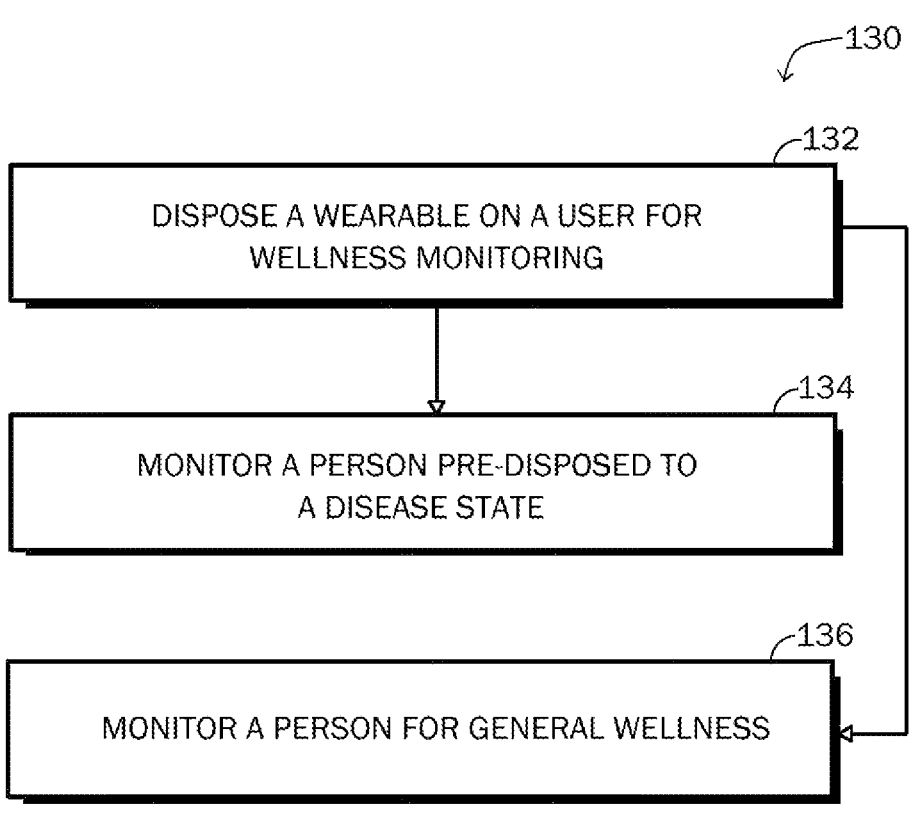
FIG. 13 illustrates an exemplary method for using a wearable in wellness monitoring applications according to an exemplary embodiment of the present invention.

Referring to FIG. 13, similar to patient monitoring above, a method 130 of the present invention may use wearable technology, disposed on a user in step 132, for wellness monitoring for persons, independent of an illness diagnosis. This may be useful to identify personal patterns and trends of the parameters for whatever purpose is desired, generally to achieve a state of wellness. Methods of the present invention may be used in persons predisposed to a particular disease state, in step 134, or may be used generally to monitor a person in step 136.

Data Acquisition with and without Feedback

Figure 14:
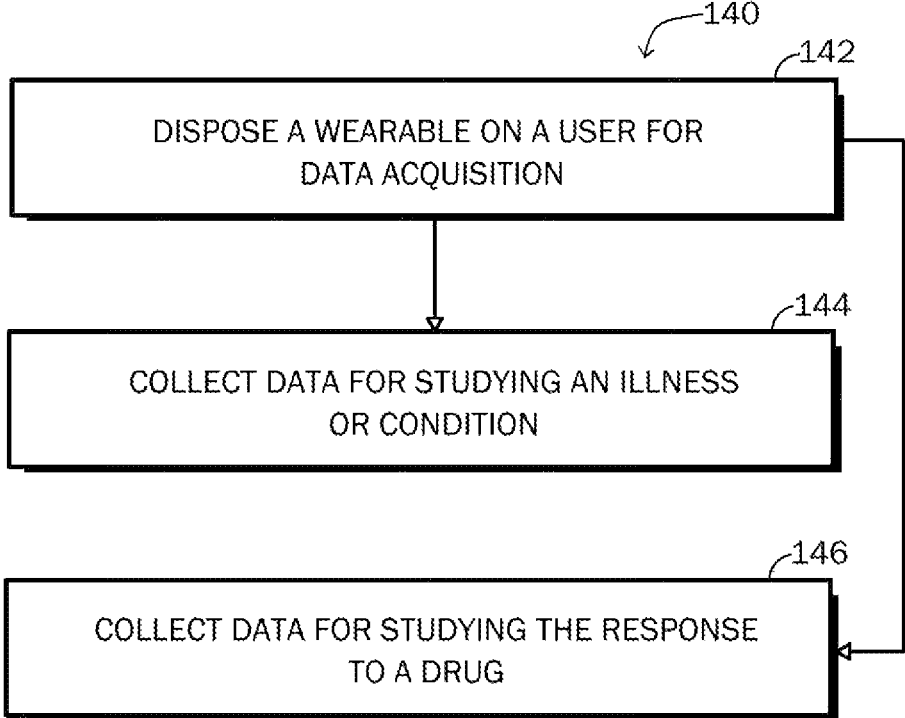
FIG. 14 illustrates an exemplary method for using a wearable in data acquisition applications according to an exemplary embodiment of the present invention.

Referring now to FIG. 14, a method 140 of the present invention can use wearable technology, disposed on a user in step 142, for the collection of parameters in the context of data that is then used for the study of an illness or condition, in step 144, in response or non-response to a drug, stimulus, or the like, in step 146. Such methods may be used in professional settings, such as at a hospital, to study a condition.

Certain methods of the present invention may be used by a clinical research organization for testing the effects of a drug or other treatment. Clinical trial centers may use wearable technology within aspects of the present invention, to measure various physiological parameters associated with the drug and/or placebo to better understand and report drug effects.

Methods of the present invention can allow for customization to a particular study to suit the type of information being collected. For example, respiration data can be monitored continuously or in response to changes to another parameter. Provisions may be made for those conducting the research to provide feedback to the user either electronically (e.g., use of algorithms) or from remote terminals, via the wearable.

Athletic Sports Monitoring

Methods of the present invention can use wearable technology for monitoring athletes and other persons participating in a sport. Monitoring may be made during rest, training, competition and post competition. This establishes a baseline and helps the user to begin getting feedback from the device when they are tending to body parameters level that are counter to a good game. For example, methods of the present invention could be used to identify if breathing affects performance. An athlete could discover, for example, that deep breaths during non-exertion during a competition enhances ability and skill level. The athlete could use this data to their advantage to improve their abilities. In some embodiments, the data collected may be time tracked so that the user can, for example, play a video of their performance in the athletic event while watching, in real time, their physiological parameters monitored by the wearable device.

In some embodiments, the methods of the present invention can use wearable technology to detect possible distress in an athlete, alerting the athlete or a coach to rest the athlete, or, in severe cases, get medical attention. In some events, especially at the high school or college level, an athlete may desire not to show signs of stress or fatigue, but instead, continue play, perhaps to the detriment to their overall health. Methods of the present invention allow coaches to detect such stress or fatigue and react accordingly.

Entertainment Physical Sports

Leagues and other sporting bodies need to begin providing additional content about the sport in order to engage the viewer and thus result in better broadcast revenue. As the sports are not changing, this additional information is tending towards anything possible about the player as well as simulations of outcome.

For example, for timed sports, the viewer can see accurate timing for the participants at various stages of the event. For example, bobsled runs may provide time checks at various points and show the user how far away the current runners are from the leader. This helps engage the viewer and adds to the overall excitement of the finish. Another use of technology used to help viewers is how in recent years, during football games, the line of scrimmage and the first down line may be marked on the field for the viewer to see.

However, as viewers become more accustomed to a particular feature or technology being used, their added excitement for viewing the sport may decline. Methods of the present invention can use wearable technology to monitor a player and provide real time data on body function that results in additional content that could generate revenue. This information could simply be displayed to the viewer or may be fed to relevant bodies to fuel betting on certain aspects, thus generating additional revenue.

For example, a user could bet that a particular basketball player would score all their points while keeping their pulse below a certain value, or the user could bet that one coach would keep their blood pressure below the other coach throughout the entire game.

Embodiments of the present invention could be used in non-physical sporting events or competitions, such as mental sporting events (chess, poker) or virtual reality or software-based gaming. For example, physiological parameters for poker players could be monitored and displayed to viewers to provide a further dimension to their play. The players themselves could later review this information to help keep their "poker face" and lessen certain tells they may be giving to other players.

Figure 15:
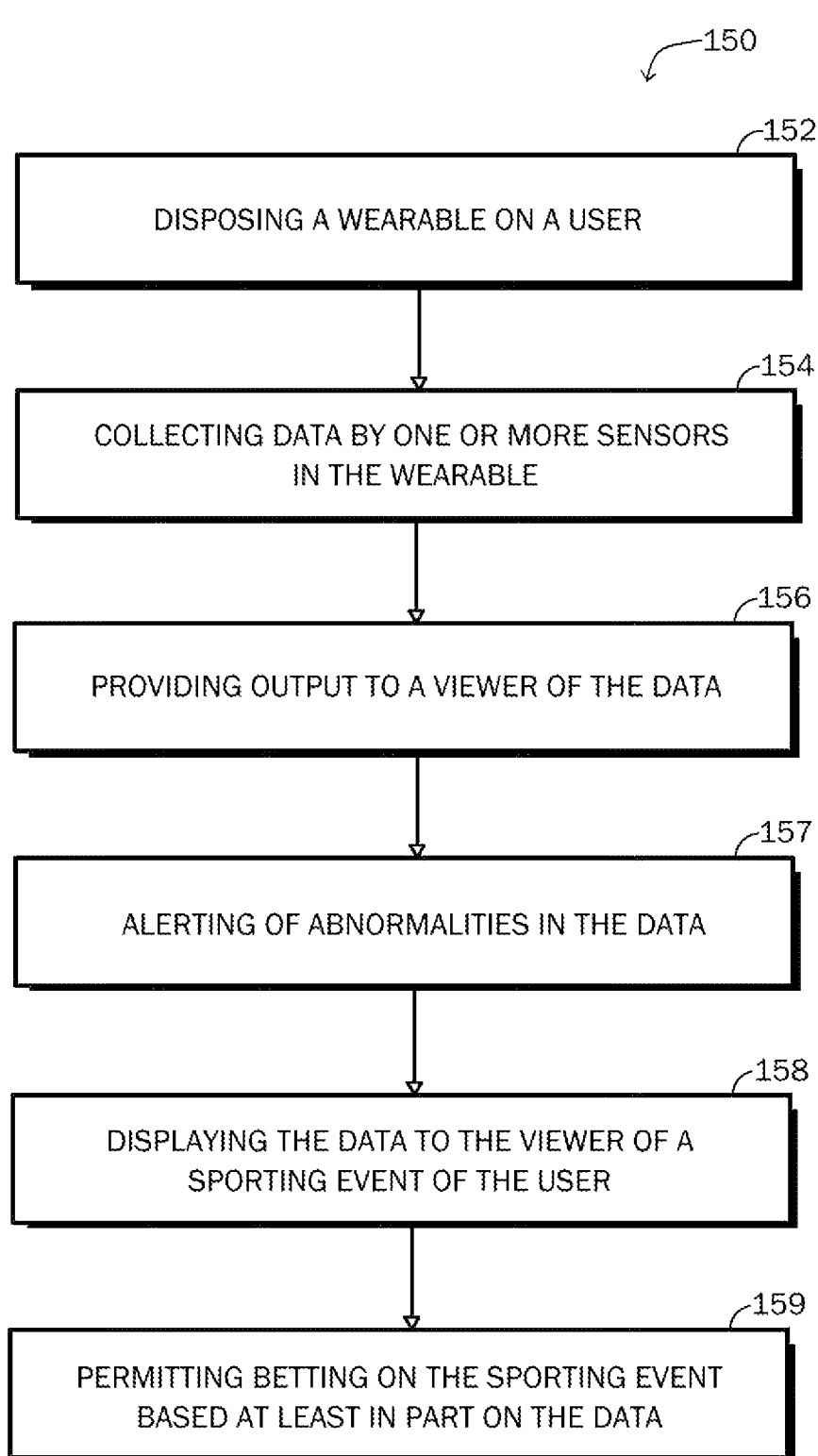
FIG. 15 illustrates an exemplary method for using a wearable in sports and athletic applications according to an exemplary embodiment of the present invention.
Figure 16:
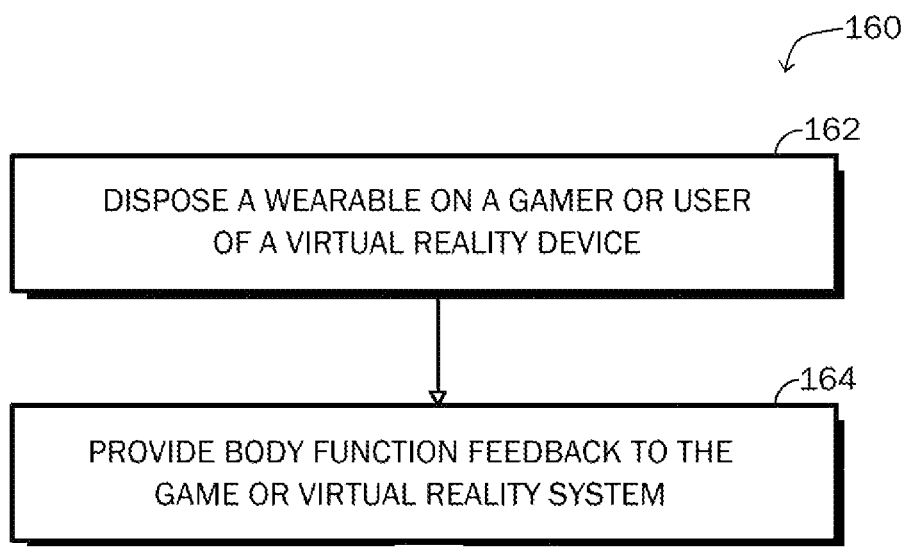
FIG. 16 illustrates an exemplary method for using a wearable in virtual reality and gaming applications according to an exemplary embodiment of the present invention.

Referring now to FIG. 15, a flow chart is shown describing a method 150 for using wearable devices according to embodiments of the present invention in the sporting and athletics field. The method 150 includes a step 152 of disposing a wearable, such as wearable 12, on a user. The wearable may be disposed at various body locations, as discussed above. The user may be, in some embodiments, a user participating in a sporting event.

Once disposed on the user, the wearable is activated and physiological data is collected by one or more sensors in step 154. The data may be collected, in some embodiments, during participation in a sporting event. The data may also be collected before the sporting event, or after the event, depending on the method. Of course, the data may be collected based on other aspects of the present invention as described above.

The output of the wearable device may be provided to a viewer in step 156. The output may be raw data sent by the wearable or may be data pre-processed or processed by the wearable. The output can be further processed by a computing device on which the viewer views the data. The computing device may provide the data in user-friendly form. For example, the data may be of a particular athlete in a sporting event and may be provided adjacent to the athlete's name or photo on the computing device.

In some embodiments, should the data be abnormal for the user's particular activity, the computing device and/or the wearable itself may generate an alert in step 157. This alert may provide a viewer of the data of a baseline value and the current, real time value of this parameter from the user, for example. For example, a football player whose pulse pressure is widening may be a result of dangerous intercranial pressure due to a head injury. Such detail could be alerted to the appropriate personnel to have the person removed from the game and examined before the condition worsens.

In some embodiments, the data can be displayed to a viewer of a sporting event, for example, on a television display, in step 158. This data may be continuously displayed or displayed at intervals to show on or more physiological measurements taken of the athlete, for example. In some embodiments, a user may be permitted to bet on the sporting event, at least in part based on the physiological measurement taken by the wearable in step 159. The display of physiological parameters and the ability to bet on such parameters adds new dimensions to sports broadcasting and the user viewing experience.

Feedback Device for Virtual Reality

Figure 17:
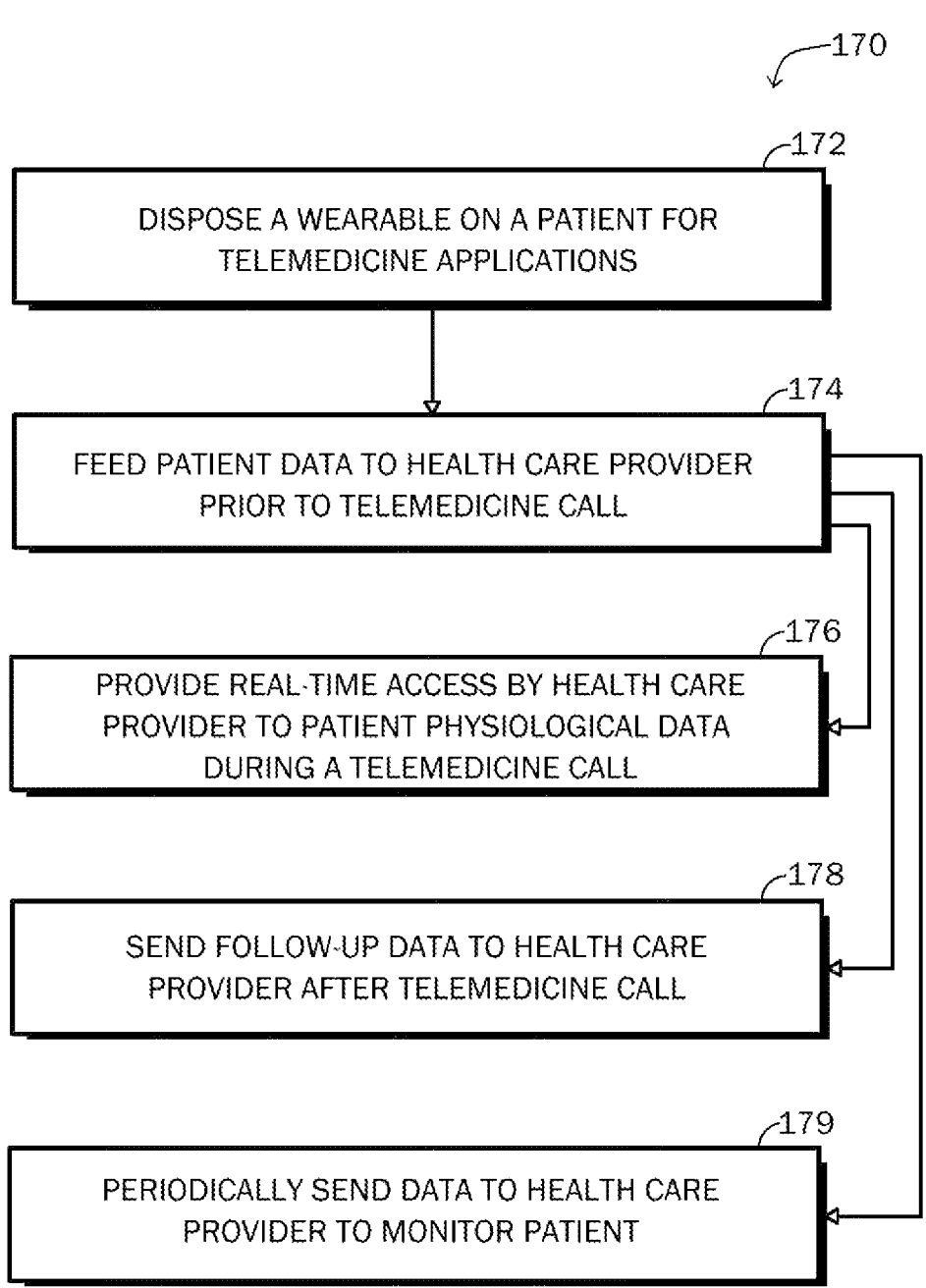
FIG. 17 illustrates an exemplary method for using a wearable in telemedicine applications according to an exemplary embodiment of the present invention.

Referring to FIG. 17, a method 170 of the present invention can use wearable technology, disposed on a user in step 172, to provide body function feedback to virtual reality and other software games in step 174. This can be used, for example, to alter the game experience to suit the state of readiness of that particular player. For example, the game could notice the player breathing irregularly, thereby resulting in the possibility of errors during a sniper shot. In some embodiments, the game may detect when a player is, for example, overly calm (via their heart rate, for example) and inject additional elements of surprise to further engage the player. In still other embodiments, certain parameters may be provided to other players to enhance their experience.

Telemedicine

Referring to FIG. 17, a method 170 of the present invention can use wearable technology, disposed on a patient in step 172, to gather data and relay this data to a healthcare provider as necessary. These methods can include three features, usable alone or in various combinations. First, in step 174, if the wearer is using the device prior to a telemedicine call, then the data can be fed to the healthcare provider, thus enhancing the diagnosis. Unlike a conventional visit to the doctor where the doctor may only see a few seconds or minutes of patient data, step 172 may include gathering patient data for an extensive period of time (e.g., days, weeks, months, even years) to be given to the healthcare provider.

Next, in step 176, during a telemedicine call, the healthcare provider can instantly access body function and physiological data that may exceed what would normally be collected during a typical office visit, thus enhancing the ability to diagnose. Third, in step 178, if the wearer continues to wear the device after a call, the healthcare provider can get follow-up information that can drive the effectiveness of the course of action prescribed.

Furthermore, methods of the present invention provide a telemedicine service that offers patient monitoring, in step 179, and can actually identify the possibility of a condition before the potential patient is aware. This service may use the wearable to collect data and send such data to a database periodically. This data is analyzed for abnormalities from baseline data. Such abnormalities may be screened against a database for possible diagnosis, or may be sent to a healthcare provider for additional follow-up. For example, the wearable device may receive data to indicate that the wearer is developing a fever, has a cough with little mucus and has shortness of breath. The device itself, via internal algorithms, or a separate computing device receiving data from the wearable, can notice these symptoms deviate from the user's baseline. This information may be sent to a healthcare provider and the user may be alerted they have non-bacterial pneumonia before they even realize they are becoming sick.

Hospital Aid

Figure 18:
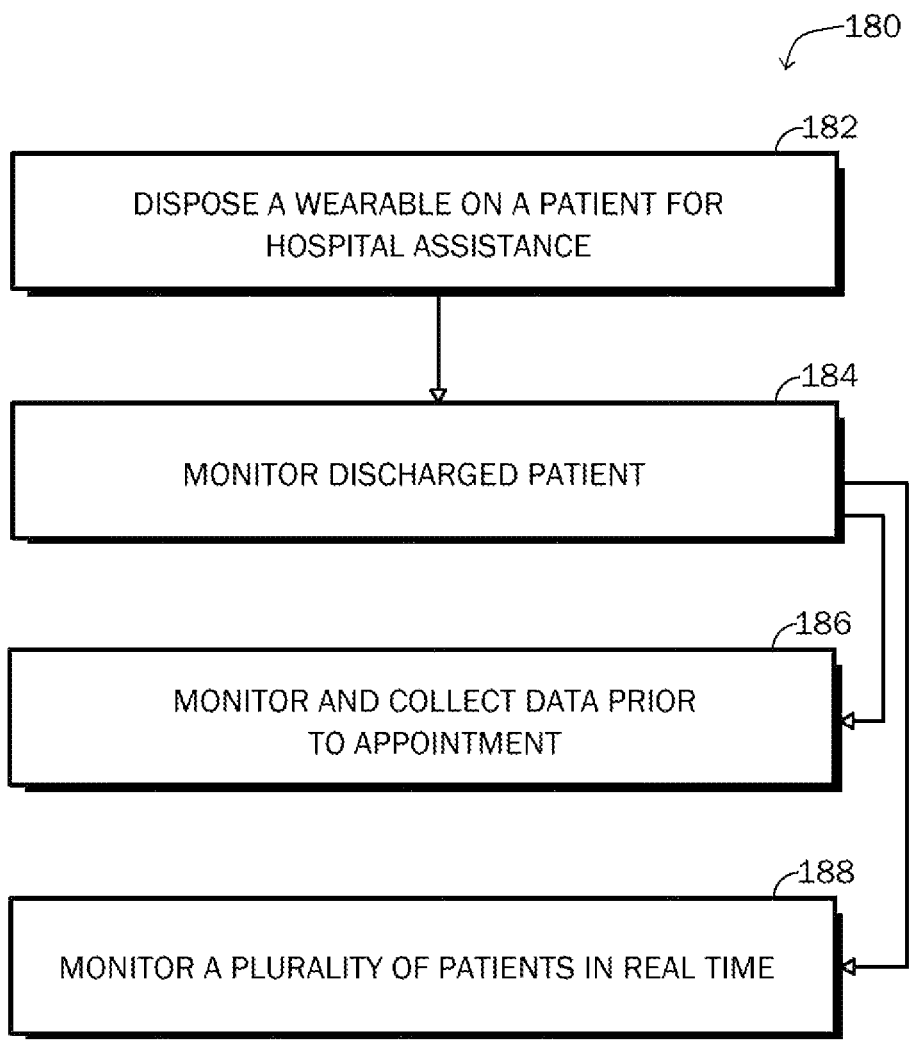
FIG. 18 illustrates an exemplary method for using a wearable in hospital assistance applications according to an exemplary embodiment of the present invention.

Referring to FIG. 18, a method 180 of the present invention can use wearable technology, disposed on a patient in step 182, to assist hospitals in various manners. Some examples of these methods are described below.

At the time of discharge from a hospital, the user can be provided, in step 184, with a wearable device to wear and continue to send information back for monitoring. This allows the hospital to identify possible relapse or other conditions which may mean that the patient would have to return to continue treatment or seek a new diagnosis.

In some embodiments, a wearable device can be provided to a patient, in step 186, for use during the period of time when they initially made an appointment to the time of the appointment, or any portion of this timeframe. This allows the healthcare provider to be aware of symptoms in detail at the time of the visit or even to prepare feedback in preparation of the visit.

In some embodiments, wearable technology can be used, in step 188, as an aid for wards which allow patients with non-life threatening conditions to continue to be monitored at a lower cost and in real time. The device could be programmed to sound an alert to indicate if an immobile person needs to be turned, or the like. In some embodiments, the device could be programmed to ask the patient to perform a certain task, such as to cough, where the device can record the cough's characteristics for later analysis.

Public Safety (Detainees and Prisoners)

Figures 19, 20:
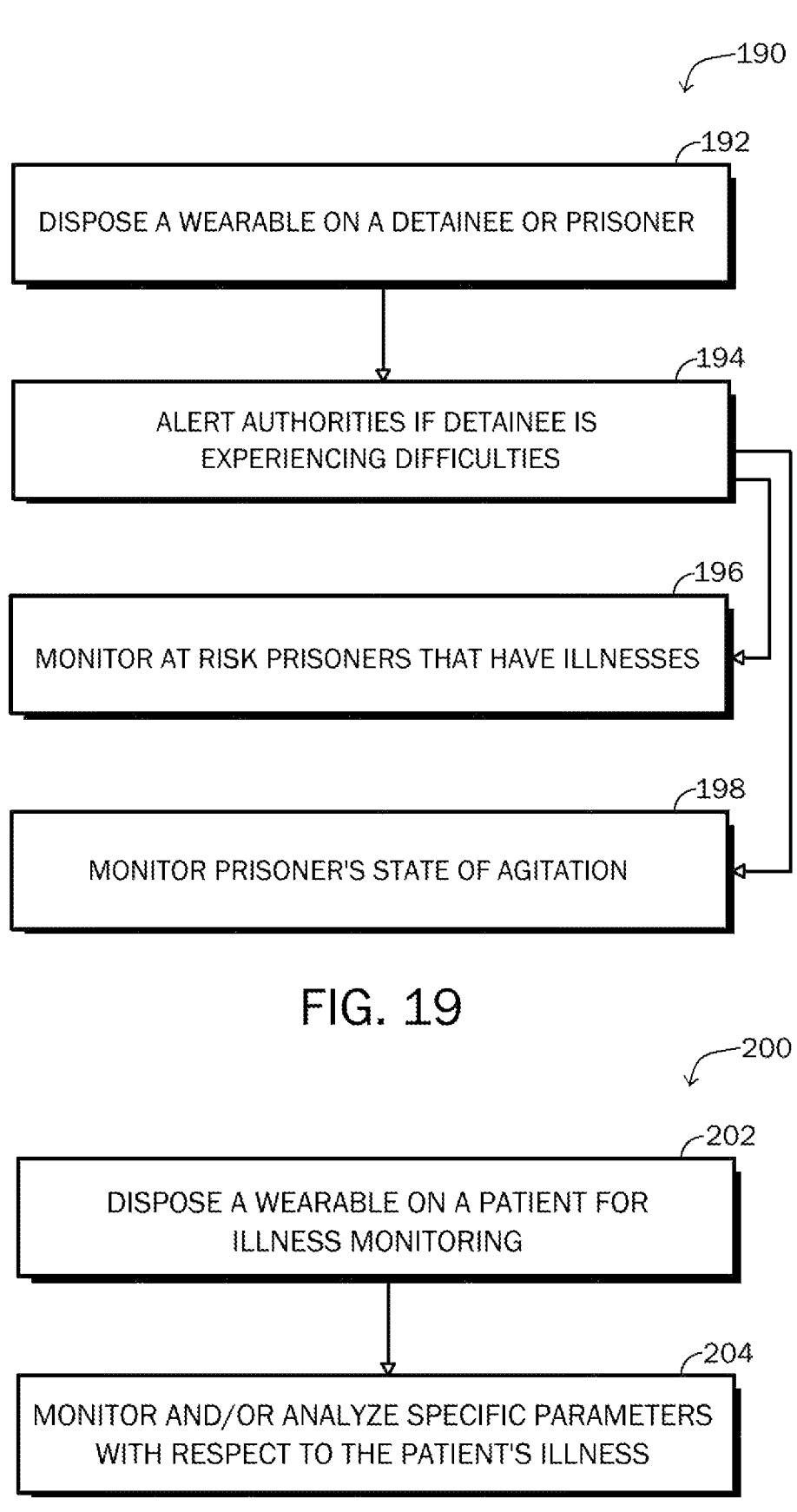
FIG. 19 illustrates an exemplary method for using a wearable in public safety/corrections applications according to an exemplary embodiment of the present invention.
FIG. 20 illustrates an exemplary method for using a wearable for illness management via monitoring one or more parameters, according to an exemplary embodiment of the present invention.

Referring to FIG. 19, a method 190 of the present invention can use wearable devices, disposed on a detainee or prisoner in step 192, in the field of public safety for detainees and prisoners. For detainees, even before enough information can be gathered about the person, especially around their health, the wearable device can be placed on them to collect data based on set points or other metrics. In this embodiment, in step 194, the authorities could be alerted when the detainee is tending to or experiencing difficulties due to current state, lack of medication, or the like.

Additionally, embodiments of the present invention can provide, in step 196, methods for using a wearable device on at risk prisoners who may have illnesses that need closer monitoring. In such cases, where it is not practical to have daily medical checkups, these methods can provide the relevant feedback.

Finally, methods of the present invention, in step 198, can use wearable devices on prisoners or detainees to monitor certain physiological parameters to not only detect the state of health of such persons, but also to detect any state of agitation. Such may be useful for correction officers to detect a potential problem, such as a prisoner fight, before it happens or at least before it can escalate and provide the appropriate response.

Illness Management

Referring to FIG. 20, a method 200 of the present invention can use wearable technology, disposed on a patient in step 202, to assist the patient and/or physician with illness management. The method 200 may be useful for various conditions, such as respiratory illnesses and/or illnesses that alter respiration, with or without a cough component. For example, the method 200 may be useful for illness management with monitoring for sleep apnea, cystic/pulmonary/idiopathic pulmonary fibrosis, and the like. The method 200 can include a step 204 to monitor and/or analyze specific parameters of the patient with respect to the patient's illness. In this aspect of the present invention, the wearable device can be used as a component in the management of one or more specific illnesses.

While the above description provides several different methods for using wearable devices, including some specific examples, it should be understood that the present invention is not limited to such specific examples. Moreover, while the above describes wearables that attach directly to the skin, other wearables, such as garment implemented wearables, may be used in certain embodiments of the present invention.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A method for measuring at least one physiological parameter from a user having a need to detect or monitor a lung cancer condition, the method comprising:

disposing a wearable on a user; and measuring the at least one physiological parameter of the user with at least one sensor disposed in the wearable, wherein the step of measuring the at least one physiological parameter provides collected data that is provided to an algorithm for detecting or monitoring a lung cancer condition, wherein the at least one sensor includes one or more acoustic sensors disposed in a protective layer to facilitates sound transfer through the housing to the one or more acoustic sensors of the wearable.

2. The method of claim 1, further comprising detecting an early acute pneumonitis by detecting a non-productive cough, fever and dyspnea on exertion by the user.

3. The method of claim 1, further comprising detecting an occurrence of severe radiation pneumonitis spreading beyond a radiation field of the user.

4. The method of claim 1, further comprising collecting physiological data to monitor for an infection before and after a treatment, wherein the treatment includes at least one of chemotherapy and radiotherapy, and the infection includes radiation pneumonitis.

5. The method of claim 1, further comprising detecting metastatic lung cancer in an already cancer-diagnosed patient.

\* \* \* \* \*